United States Patent [19]

Kantar et al.

[11] 4,164,875

[45] Aug. 21, 1979

[54] APPARATUS FOR MATCHING SKIS

[76] Inventors: Anthony M. Kantar, 6495 Barrie Rd., Minneapolis, Minn. 55435; George E. Pribyl, 5106 W. 105th St., Minneapolis, Minn. 55437

[21] Appl. No.: 887,484

[22] Filed: Mar. 17, 1978

[51] Int. Cl.² ............................................. G01N 3/20
[52] U.S. Cl. .................................................... 73/812
[58] Field of Search ............................ 73/100, 89, 812

[56] References Cited

U.S. PATENT DOCUMENTS

| | | | |
|---|---|---|---|
| 2,693,107 | 11/1954 | Paden | 73/100 |
| 3,922,908 | 12/1975 | Stemsrud et al. | 73/100 |

FOREIGN PATENT DOCUMENTS 2512279  10/1975  Fed. Rep. of Germany ............. 73/100

*Primary Examiner*—Anthony V. Ciarlante
*Attorney, Agent, or Firm*—Schroeder, Siegfried, Ryan, Vidas & Steffey

[57] ABSTRACT

This invention relates to an apparatus for testing and matching a pair of cross-country skis. The apparatus measures the weight of the potential user and compares this weight with the force required to bring each ski of a pair to a degree of flatness required to obtain satisfactory gripping area on the ski. The apparatus also provides an arrangement for identifying the extent of the gripping area and distinguishes the same from the sliding areas of the skis so that they may be readily identified for the application of various waxes thereto with different skiing conditions.

16 Claims, 5 Drawing Figures

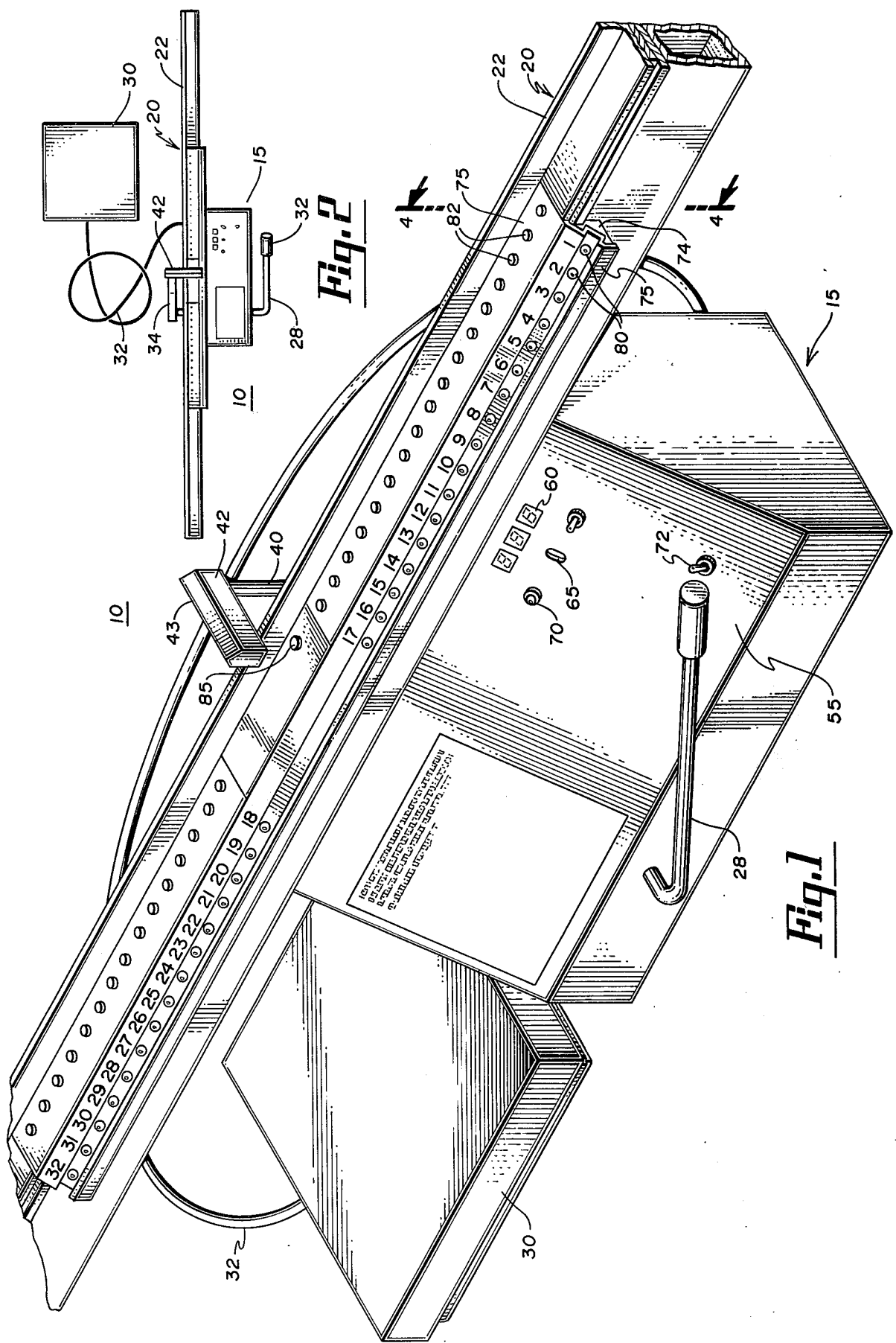

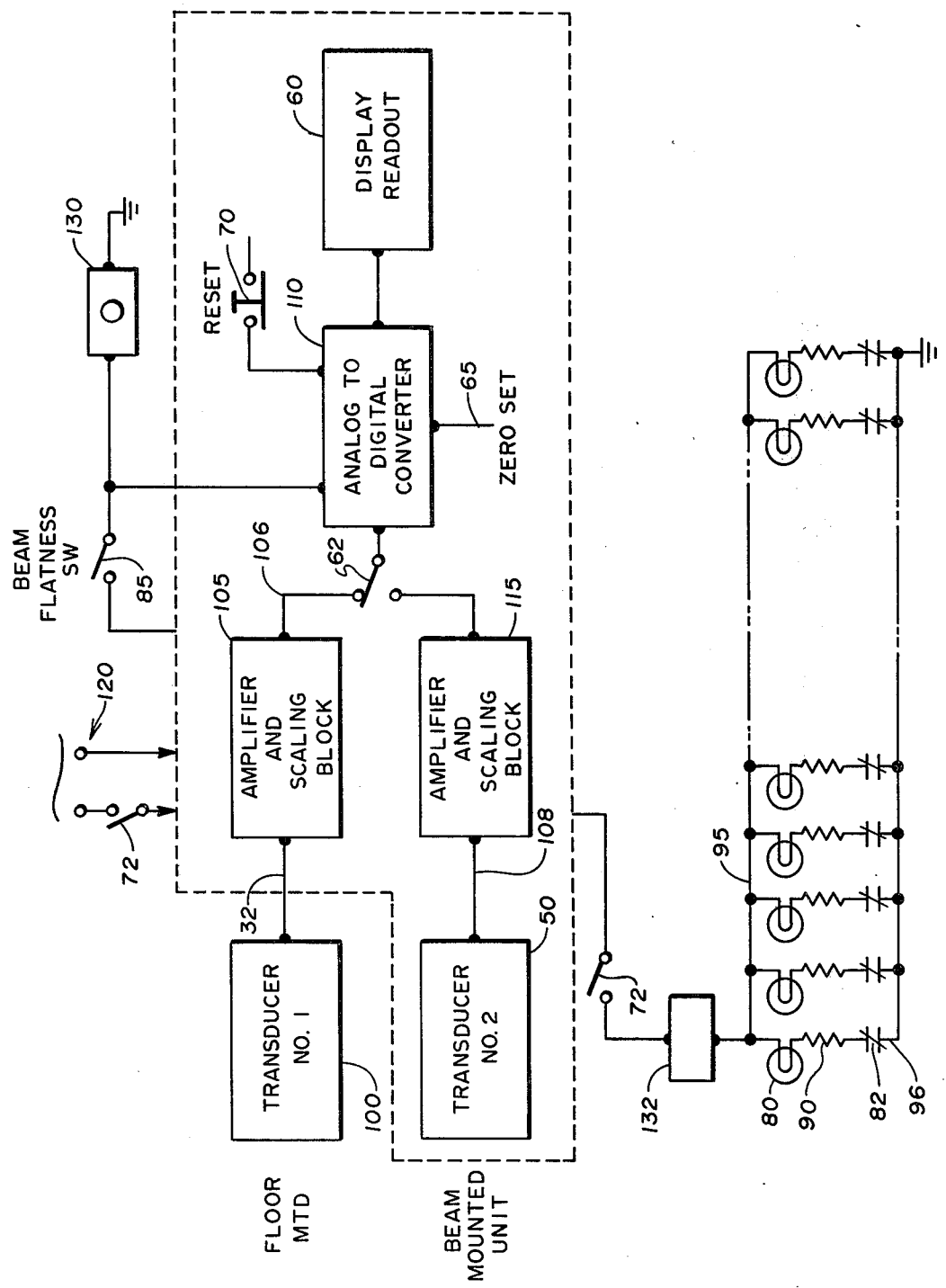

APPARATUS FOR MATCHING SKIS

FIELD AND BACKGROUND OF INVENTION

This invention relates to an apparatus for testing skis and more particularly to an apparatus for matching skis which are bowed along their extent, such as downhill and cross-country skis, to the weight of a user and one ski of a pair to the other.

Skis are customarily matched by selecting a length of a ski to correspond to the height and approximate weight of the user together with the experience or agility of the user and the type of skiing expected to be encountered. In the case of jumping and various types of downhill skis, such a match is ordinarily sufficient to obtain the desired operating characteristic from the ski. In the case of cross-country skiing, individual skis are constructed of a high degree of camber or bow along their extent, and the weight of the user or the force applied to the ski in skiing significantly effects the operating characteristics of cross-country skis. Thus, in the selection of cross-country skis, it is particularly desirable to match the skis or the flexure of the same with the weight as well as the height of the skier for optimum ski performance. Such cross-country skis when manufactured do not always have the same degree of flexure or stiffness, and consequently, such skis are not necessarily matched to one another for optimum skiing performance.

In the use of cross-country skis, it is well recognized that the front and rear bottom areas of the ski will primarily be used for the gliding portion of the skiing stroke and, consequently, should have the lowest coefficient of friction for the surface over which the ski is traversing. The intermediate portion of the ski on the kick or power stroke conversely should have the highest coefficient of friction for optimum performance. Further, in the use of cross-country skis and in particular, during the glide portion of a skiing stroke, the intermediate area of the ski should be clear of the surface being traversed. In the kick portion or power portion of the stroke, the intermediate portion of the ski should be in contact with the surface being traversed. To obtain the desired frictional surfaces, the various areas of the ski are selected for the application of different waxes. In addition, different types of weather conditions, such as powder snow, wet snow, or hard track dictates the use of different types of wax to be applied to these portions of the ski for optimum ski performance. Similarly, the portions of the ski in contact with the surface during different portions of the skiing stroke will alter in length under such conditions. Thus, it is necessary to match cross-country skis to the weight and, hence, the force the skier will apply to the ski during skiing. Further, it is desirable to know from the flexure of the ski which areas of the ski surface will be in contact with the ground or surface being traversed at different portions of the skiing stroke. This will enable the user to mark on the surface of the skis the general location of contact areas so that different types of waxes may be readily applied thereto for the different skiing conditions.

SUMMARY OF PRESENT INVENTION

The present invention is directed to an apparatus for matching a pair of skis having a high degree of camber, such as cross-country skis, to the user of the same. The improved apparatus senses and displays the user's weight and compares the weight with a force required to bring the ski into varying conditions of flexure and ultimately flatness to identify the areas of the ski used under optimum skiing conditions. The apparatus includes a frame which mounts an elongated beam structure having a length sufficient to accommodate the length of the ski. The frame mounts a reciprocating pressure rod having an overhanging pressure pad which is moved toward and away from the beam surface midway along its extent for the purpose of flexing a ski thereon. The pressure rod and pad are moved through a lever which is pivotally mounted on the frame and coupled to the pressure rod through a force sensing transducer. The pressure pad mounted on the pressure rod and positioned over the beam has a balance edge thereon so that the balance point of a ski may be determined and referenced to the pressure pad when the ski is flexed to determine the operating characteristics of the ski for varying weights or forces applied thereto. Associated with the frame is a scale by means of which the weight of a potential user may be measured and indicated for the purpose of matching the skis and particularly the flexure of the same to the user. An indicator on the frame displays not only the weight of the user, but also through the switching circuit, displays the force applied to the ski through the pressure pad. This enables the operator to determine the weight required to flex the ski to its ultimate position of flatness with respect to the beam and also to measure the degree of flexure for varying forces applied thereto. The beam has a plurality of switches each having an associated indicator adjacent thereto which are distributed along the extent of the beam to either side of the reference point determined by the overhang of the pressure bar. The switch and lights will be operated upon flexure of the ski to determine the extent of flexure of the ski for varying forces applied thereto. In addition, the beam includes a sensor and indicator to indicate complete flexure of the ski.

The force applying structure on the beam which flexes the ski being tested, and the indicator structure associated therewith enables an operator to a match of ski flexure with the weight of the user to determine whether the ski will have optimum operating characteristics. Similarly, the degree of flexure between the tip and tail ends of the ski as varying forces are applied thereto will permit making of the skis to indicate the various surfaces of the ski in contact with the surface being skied on for varying conditions of operation of the ski. This will identify the areas of the ski to which special waxes will be applied for optimum operating characteristics.

DESCRIPTION OF THE DRAWINGS

FIG. 1 is a perspective view of the improved apparatus for ski matching of the present invention;

FIG. 2 is a plan view on a much smaller scale of the apparatus of FIG. 1;

FIG. 5 is a schematic block diagram of the force measuring portion of the improved apparatus, and includes a schematic circuit diagram of the flexure indicating portion of the apparatus.

DESCRIPTION OF THE PREFERRED EMBODIMENT

Our invention in an apparatus for testing of skis is shown generally at 10 in FIG. 1. This apparatus is comprised of a base or frame structure 15 upon which is mounted an elongated beam structure 20 designed to mount and test the flexure of a ski. Included with the apparatus is a floor type scale 30 designed to sense and indicate the weight of the user of the skis being tested to correlate the weight or force applied to the ski to the particular flexure of the ski being tested.

Figure 3:
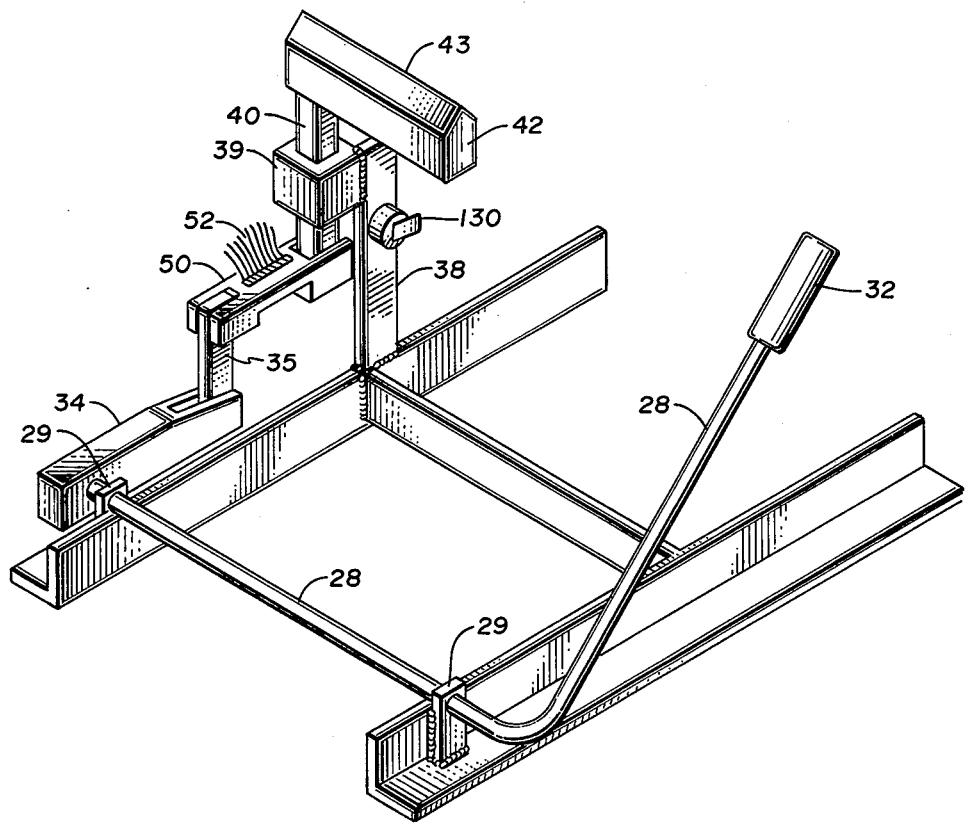
FIG. 3 is a perspective view of part of the frame portion of the apparatus of FIG. 1 showing the means for applying force to a ski to flex the same.

The frame or base 15, as will be best seen in FIG. 3, has a weldment type support structure 25 formed of angle iron suitable welded together to mount the remaining portion of the enclosure for forming the frame. A lever 28 is journaled on the support structure through bearing blocks 29 suitably welded to the support structure. The lever has a handle 31 extending from one end of the same which is positioned outside of the frame structure as will be seen in FIGS. 1 and 2. The other end of the journaled lever mounts a lever arm 34 to which is attached a pivoted linkage 35. An upstanding flange member 38 is also attached to the support structure 25 intermediate its extent, and the free end of the flange member mounts a bearing block 39 in which is positioned a slidable pressure rod 40. Attached to the end of the pressure rod is a pressure bar 42 which extends normal to the pressure rod and has a knife or balance edge 43 on the top side of the same with a suitable rubber cushion (not shown) on the bottom side of the same. The opposite end of the pressure rod mounts a beam type transducer 50 which transducer is secured at one end of the pressure rod and at its opposite end to its linkage 35. The transducer 50 includes suitable energizing and sensing windings indicated generally at 52, and, as will be seen in FIGS. 1 and 2, the pressure rod 40 extends alongside the frame structure 15 with the pressure bar 42 thereon being positioned over the beam structure 20 on the frame 15.

The frame 15 with its enclosure has an inclined face 55 with the elongated beam structure 20 being positioned on the top of the frame. The frame mounts an indicator 60 which has a plurality of digital indicia exposed through openings in the face 55 of the enclosure. A selector switch 62 is positioned within the enclosure and it has an operating toggle extending through the face 55 of the frame. Switch 62, as will be later noted, selects one or the other of a pair of circuits to be displayed on the indicator 60. A portion of the zero adjust knob 65 also projects through the face 55 of the enclosure as does the button for a reset switch 70. The face of the enclosure also mounts an on/off switch 72 whose toggle extends through the face for operation of the switch. The inclined face 55 of the frame enclosure also mounts a reference chart 80, the purpose of which will be later noted. The operating handle 32 of the pivoted lever extends adjacent the face 55 of the frame so as to be readily accessable to the operator of the apparatus in the sensing and testing of skis.

Beam structure 20 is an elongated structure which is suitably secured to the top surface of the frame 15 through means, not shown. The beam has a length slightly longer than the length of the skis to be tested and the pressure bar 42 is positioned over the beam and offset approximately 5" from the center of the beam.

The beam structure 20 may take varying forms, and where the term beam structure is used herein, it will include any structure which will support a ski at its tip and tail ends with appropriate intermediate parts which define a planar reference with the tip and tail supports and which will support the switches to be hereinafter defined in a plane with the tip and tail of a ski.

Figure 4:
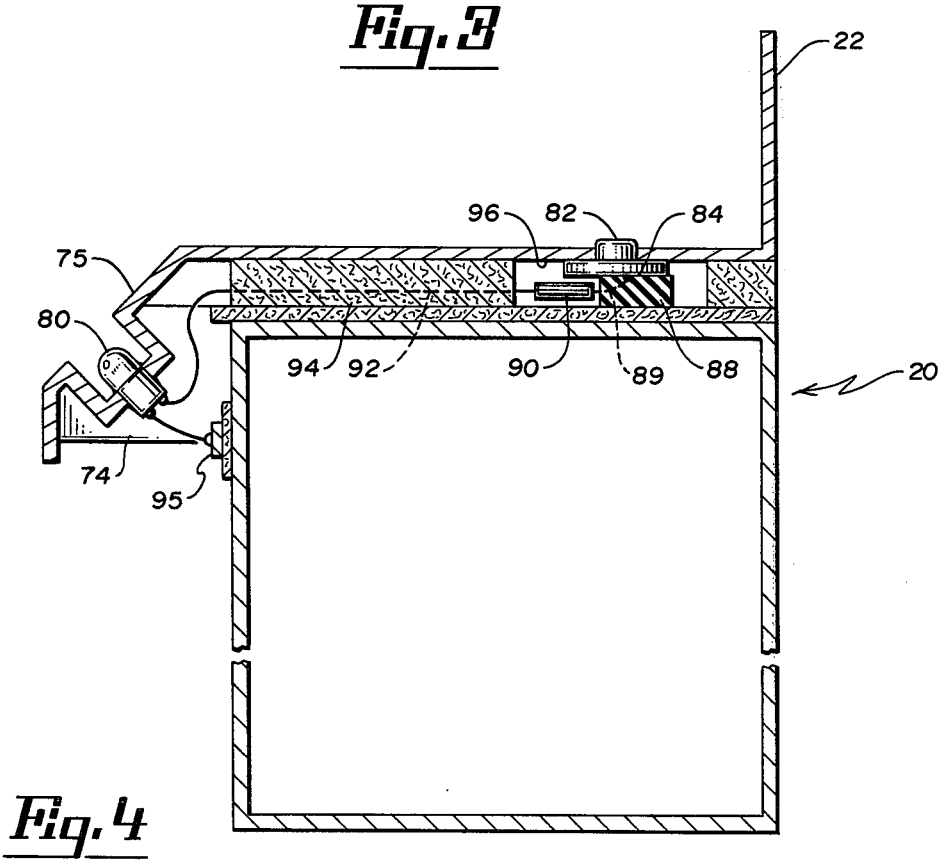
FIG. 4 is a sectional view of the apparatus of FIG. 1 taken along the lines 4—4 therein and with parts broken away.

As will be best seen in FIGS. 1, 2 and 4, the beam 20 is formed of a generally rectangular cross section and it includes an upstanding rib 22 at the edge of the same adjacent the pressure rod 40 and extending the extent of the beam to serve as a guide for a ski being tested thereon. The opposite or front side of the rectangular beam has a flange member 74 extending along the face of the beam adjacent the inclined face 55 of the frame 15. A plate 75 is positioned over the flange member and and a plurality of indicating lights 80 are distributed along the extent of the same. Each indicating light has an associated switch button 82 positioned in the face of the beam adjacent thereto and aligned with the respective indicator light. The switch buttons 82, as will be best seen in FIGS. 1 and 2, are distributed along the extent of the beam which cover the normal area of camber of the ski positioned thereon between the tip extremity and the tail extremity of the ski. A spacing in the plate 75 between these switches is located beneath the pressure bar 42 which is related to the balance point of the ski. A single switch 85 is positioned in a raised portion in the beam at this point, which switch is operated by the ski when it is flattened against the center portion of the beam indicating complete flexure of the ski from tail to tip as the ski is depressed. The area in which the switch buttons 82 are positioned are covered by the portion of the plate 75 which extends over the top of the beam.

As will be seen in FIG. 4, the individual switches are formed of a button 82 having a contact pad 84 attached thereto which is made of a conducting material. The contact pad rests on a compressible rubber cushion 88 which holds the pad against the plate 75. A lead connector 89 extends from the contact pad 84 to a resistor 90 with a lead wire 92 extending therefrom and through insulating members 94 on the top of the beam. The lead wire 92 is connected to one terminal of the lamp 80 and the other terminal of the lamp is connected to a power supply bar indicated by the connection 95. The undersurface of the plate 75 has a conductor material 96 thereon, and a circuit is formed between the conductive material 96 of the plate 75, which is grounded, and the contact pad 84 of the button switch to form a normally closed switch which is biased to the closed position by means of a rubber cushion 88. The conductive surface 96 is the common ground for all of the indicator lights along the extent of the beam. One terminal of each light is connected to the common bus 95 which is energized. Power to the bus is controlled by switch 72 with each light being connected through a switch formed by the conducting surfaces formed by the pad 84 and of surface 96 on plate 75. Thus, the indicating lights will be energized and will go off or be de-energized whenever a button 82 is depressed to break the circuit between the conducting surfaces for each switch. As also will be seen in FIGS. 1, and 2, the scale 30 is connected by means of a cable 32 to the base frame and circuit components therein, as will be hereinafter noted.

FIG. 5 shows a schematic block diagram of a portion of the improved apparatus. Scale 30 includes a transducer 100 which provides a signal output connected through the cabling 32 to a sensing amplifier and scaling block 105. The output circuit therefrom is evidenced by the conductor 106 which is connected through the beam floor selector switch 62 to an analog to digital converter 110. The output of the converter operates a display unit, indicated in block at 60, which is shown as the digital display on the face of the frame 15. The beam mounted transducer 50 is operated by the lever 28 applying force to a ski positioned on the beam. It provides a signal output, in terms of a force applied to the lever, through a conductor or cabling 108 to a second amplifier and scaling block 115, the output of which is connected to the other terminal of the selector switch 62. A suitable power supply 120 is indicated in block with the on-off switch 72 in circuit therewith to control the application of power to the control block. Sensing switch 85 is connected from the power side of the control block to the input of the converter 110 for the purpose of holding a reading on the digital display unit 60 and to sound an audible alarm 130 mounted on the frame to indicate that the ski has reached a flattened state. The reset button 70 in the control will reset the converter 110 after the display is no longer needed. In addition, the zero adjust knob 65 provides an adjusting signal to the converter to zero the display unit. The structure in the control block is a unit manufactured by Centech Corporation, Minneapolis, Minnesota and is identified as Agri-Electronic Electro Weigh Pak. Further, the scale and its transducer 100 is a conventional unit manufactured by Heath Kit Corporation of Benton Harbor, Michigan, which has the Type No. GB1186.

As will be seen in FIG. 5, the flexure contact switches on the beam are energized from the power source of the control circuit through an adjusting regulator 132 with the contacts of the on-off switch 72 in circuit there with. The output of the regulator adjusts the voltage to be applied to the light emitting lamps 80 through the bus 95 which is connected to one side of each of the lamps. The switches, shown generally at 82, are connected in series circuit with each of the lamps. The switches are formed by the conductive undersurface 96 of the plate 75 positioned on the beam and the conductive pads 84 of each button switch. The current limiting resistors 90 are included in each circuit to adjust the voltage applied to the lamps. With each switch 72 on, the control circuit is energized and each of the indicating lamps will be energized.

In the operation of the improved apparatus for sensing or measuring flexure of a ski, a pair of skis, such as cross-country skis or other skis with significant camber are selected in terms of the height and approximate weight of the user. The accuracy of the weight is determined by the individual stepping on the scale with the read out of the same being obtained on the indicator on the face of the apparatus. Thus, based on the user's weight and the force required to bring the ski to a degree of flatness required to obtain satisfactory gripping, that is in the center contact area, the skis will be matched to a user.

In the use of the apparatus, the display unit will first be set at zero reading and the selector switch 62 will be adjusted so that it can selectively connect one or the other of the transducers 50 or 100 the display unit to read either the weight of the user as he steps on the scale 30 or the force applied to the lever arm or handle 31 to move the pressure bar against the ski. The amplifier and scaling blocks adjust the level of signal output therefrom so that the display unit will read in terms of proper units.

After measurement of the user's weight, reference to the individual's weight and height on the chart 80 on the face of the instrument or apparatus will enable the selection of the basic ski length for matching. One ski of a pair is selected and placed on the balance edge 43 on top of the pressure bar to determine the balance point along the length of the ski. Upon finding of this balance point, a reference point is marked on the ski approximately 5" toward the tail end of the ski from the balance point. The ski is then placed on the beam such that the reference point noted is now located directly below the pressure bar 42. The ski is then tested by applying downward pressure on the pressure bar 42 through movement of the handle 32. This will apply a force through the linkage arm 35 to the pressure transducer 50 which is connected to the pressure rod 40 and the pressure bar 42. The pressure bar 42 moves down to apply pressure to the top surface of the ski being tested, which is positioned on the beam along the flange 22 thereon. With the selector switch 62 in the beam position, the readout of pressure applied to the ski will be shown on the indicator 60. Increasing the amount of force applied to the lever will cause the ski to bend to a degree of flatness which will operate the sensing switch 85 at the center of the beam beneath the pressure bar. This will sound the audible alarm 130 mounted on the flange 38 on the instrument frame. The switch 85 sets a hold function on the converter and the display unit will display the force required to flatten the ski. The reading of the force required to reach this point will be noted on the reference chart and an operator will determine whether or not the deflection force required falls within the recommended range based upon the perspective user's height and weight combination listed on the reference chart. The reset switch 70 in the circuit is then operated to return the indicator to zero. The second ski of the pair is tested in a similar fashion to determine the amount of force required to flatten this ski and whether this force matches that noted for the first tested ski. If the force required falls within a very limited range of the first force, than the skis will be found to be matched. In the event that the match does not occur, another pair of skis will have to be used.

Since the manufacturing process used in producing skis varies from manufacturer to manufacturer, and in some cases within the same production facility of a given manufacturer, a different response force to varying pressures may be evident, even though the pairs are identified as being of the same length and camber. It is therefore advantageous to test the skis of each pair to determine their response to a person's weight equally distributed between them and to further identify the length and location of the bottom areas of each ski which will be in contact with the surface being skied on during different snow conditions. These areas require the application of different waxes for different snow conditions.

Thus, after the match of the skis to the individual is obtained, the lever arm is again operated with varying force applied. As the ski with the camber deflects toward the beam, the indicator lights operated by the buttons on the beam will shut off as the ski contacts the respective buttons distributed along the extent of the beam. In determining the areas for waxing, a percentage of force equivalent to the user's weight is applied to the ski and as the series of numbered indicator light which normally are illuminated with no pressure applied begin to turn off, the areas of contact toward the tail and tip end of the skis will be noted. Upon reaching a percentage of the user's weight, the operator of machine will note the number of the last indicator light which goes out towards both the tip and tail end of the skis and he will release the operating lever and mark the skis at these points. More than one pair of marking per ski may be used and these markings generally cover the range of waxing necessary between powder snow conditions (greater length) and hard snow or track snow which is of a shorter length. This will enable the user of the ski to identify the areas of the ski which normally are in contact with the ground during certain modes of skiing, such as gliding, and will permit the application of a different type of wax thereto and to the center or gripping portion of the ski.

In consideration of this invention, it should be remembered that the present disclosure is illustrative only, and the scope of the invention should be determined by the appended claims.

What we claim is:

1. An apparatus for matching skis to the user and one of the pair of skis to the other, comprising: an elongated beam structure positioned on a frame and adapted to have a ski positioned thereon, pressure applying member movably mounted at a fixed location on the frame and movable toward and away from the beam structure to contact a ski thereon and flex the ski transversely while the ski is held against longitudinal movement relative to said frame, means including a pivoted lever mounted on the frame and connected to the pressure applying means to move the same, transducer means associated with said last named means to measure the force on the pressure applying member in flexing the ski at various positions along its length and means located along the length of the beam structure to indicate the extent of transverse flexure thereat while the ski is so held and flexed by said pressure applying member.

2. The apparatus of claim 1 and including indicator means mounted on the frame and connected to said transducer means to indicate the force applied through the pressure applying member to flex a ski on the beam.

3. The apparatus of claim 1 and including a platform scale assembly adapted to indicate the weight of a user and connected to the indicator means on the frame of the instrument to display the same.

4. The apparatus of claim 3 and including switching circuit means mounted on a frame and selectively connecting a platform scale assembly and the transducer means to the indicator means positioned on the frame.

5. The apparatus of claim 1 in which the means distributed along the extent of the beam structure is a plurality of switches each having a light associated therewith with said switches and lights being located to either side of the pressure applying means and each adapted to be selectively operated throughout contact of the skis on the beam structure with flexure of the ski.

6. The apparatus of claim 5 in which the plurality of switches distributed along the extent of the beam structure have the associated lights positioned on the face of the beam structure adjacent the respective switch to indicate contact of the ski with the switch at a particular point along the extent of the beam structure.

7. The apparatus of claim 1 in which pressure applying member is a pressure bar slidably mounted in the frame and connected to the pivoted lever.

8. The apparatus of claim 7 in which the transducer means associated with the last named means is a beam type transducer coupling the pivoted lever to the slidably mounted pressure bar.

9. The apparatus of claim 7 in which the pressure bar has a balance edge positioned on the top edge of the same adapted to have a ski positioned thereon for determining the balance point of the ski.

10. The apparatus of claim 7 and including means mounted on the beam structure beneath the pressure bar and responsive to contact with the ski when flexed thereon to indicate a condition of contact of the ski along its extent with the beam.

11. A system for matching a pair of cross-country skis which are bowed along their extent to a user and one ski of the pair to the other, comprising: a beam structure, means on the beam structure for determining the balance point of a ski; means mounted at a fixed location on the beam structure for applying a transverse force only in the area of the balance point of a ski to a ski held in a position against longitudinal movement on the beam structure; and indicator means located at various points along the length of said beam structure for indicating the force required to flex the bowed ski transversely to a position of contact with the beam structure at various positions along the extent of the ski while the latter is held in such position.

12. The system of claim 11 and including means positioned on the beam structure for indicating the areas of contact of the bowed ski with the beam structure with varying forces applied to the ski on the beam structure.

13. The system of claim 12 in which the means positioned on the beam structure for indicating the area of contact of the bowed ski are switches with adjacent indicating lights positioned along the extent of the beam structure.

14. The system of claim 12 and including means to determine the weight of a prospective user of a pair of cross-country skis to be tested on the beam structure, said weight-determining means being selectively connected to said indicator means.

15. The system of claim 14 and including means on the beam structure to relate the weight of the prospective user of the ski to the force in the area of the balance point of the ski required to flex the ski into contact with the beam structure along its extent.

16. The system of claim 11 in which the means for applying a force to the ski in the area of a balance point of the ski includes a lever connected to a pressure bar which is slidably mounted on the beam structure and movable relative to the beam structure to contact the ski, said lever being connected to the pressure bar through a force indicating transducer.

* * * * *